July 15, 1958 V. B. RODGERS Plant Pat. 1,730
ALMOND TREE
Filed Nov. 29, 1957
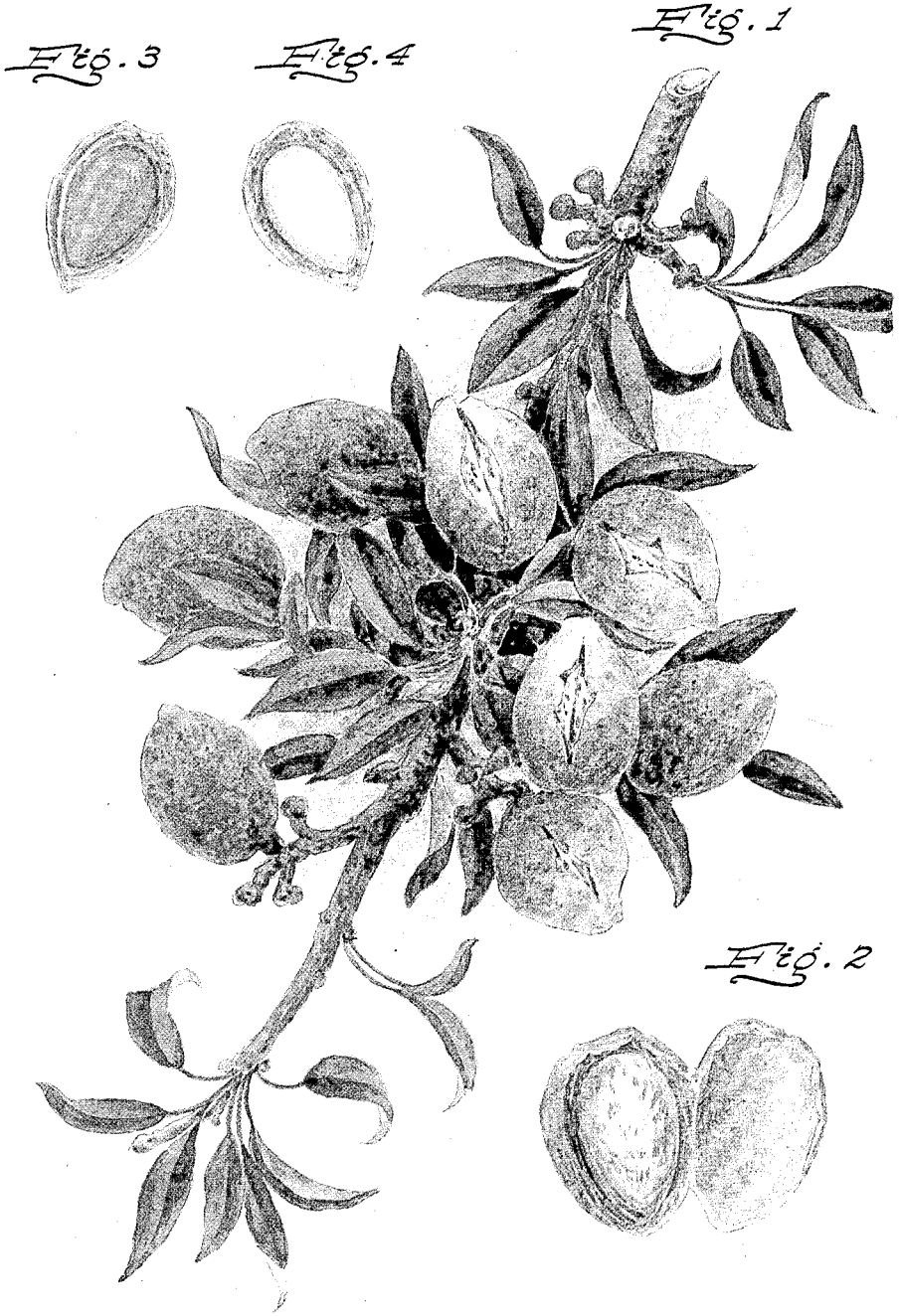
WITNESS
Addison E. Avery
INVENTOR
Vincent B. Rodgers
Webster & Webster
ATTYS.

United States Patent Office

Plant Pat. 1,730
Patented July 15, 1958

1,730

ALMOND TREE

Vincent B. Rodgers, Ballico, Calif.

Application November 29, 1957, Serial No. 699,878

1 Claim. (Cl. 47—62)

This invention relates to a new and distinct variety of almond tree which was originated by me as a seedling derived from a cross of the Mission almond (pistillate parent) and the Nonpareil almond (stamenate parent); the cross having been made, and the seedling brought into maturity, on my ranch located near Ballico, California.

The Mission and Nonpareil almonds are unpatented.

As the parent tree of the present variety evidenced certain desirable characteristics for commercial growing, it was asexually reproduced—for the purpose of comparison and further observation—by June buds on S-37 root stock (United States Plant Patent No. 904). Such reproductions, initially made on my behalf by a nursery at Modesto, California, were subsequently replanted and grown to maturity on my ranch located as aforesaid, and where the reproductions were found to run true to the parent tree in all respects.

The distinctive characteristics of the present variety of almond tree can best be recognized in comparison to the Nonpareil almond—which in general it most nearly resembles—as follows:

The tree of the present variety—which is vigorous and upright in growth—is a very heavy producer of commercially high-grade, paper-shell nuts, with the quality no less than—and the production averaging at least twice as much as—that of the Nonpareil almond; the nuts being well sealed, and hence resistant to damage by insects, such as the navel orange worm. Additionally, the nut is considerably lighter in color (very light straw) than the Nonpareil, and consequently is very attractive for market sale unshelled.

By further comparison, the variety here claimed ripens with and after the Nonpareil almond, and the harvest immediately follows the latter. As the ripening period as well as the harvest are relatively early as compared to numerous other varieties, the possibility of storm damage is minimized.

By still further comparison, the present variety and the Nonpareil almond can be planted in alternate orchard rows and act to pollinize each other; thus avoiding the need of pollination from other and less desirable varieties of almonds.

Of advantage also is the fact that the two varieties bloom contemporaneously, which is favorable economically as frost prevention measures by smudging or otherwise, when undertaken, simultaneously protect both varieties.

In the drawings:

Fig. 1 is an elevation illustrating, on a twig, both leaves and nuts; certain of the latter being shown as partially open.

Fig. 2 is an elevation of one of the nuts with the hull open.

Fig. 3 is an elevation showing a kernel remaining in half of the shell.

Fig. 4 is a similar view, but shows the kernal half cut away to expose the meat.

Referring now more specifically to the botanical details of this new and distinct variety of almond tree, the following is an outline description thereof; all major color plate identifications being by reference to Maerz and Paul Dictionary of Color:

Tree:

*Density.*—Open.

*Size.*—Medium.

*Vigor.*—Vigorous.

*Branching habit.*—Upright.

*Color of bark.* — Mature bark — brown. New shoots—green, turning reddish.

*Foliage.*—Abundant. Leaves: Size—average length, 67⅖ mm.; average width, 19 mm. Shape—lanceolate. Margin—slightly crenate. Color—top side—medium green (23–L–5), with some yellow shading; under side—slightly lighter green (22–J–5).

*Bloom.*—Amount of bloom—very heavy. Blooming period—parallels the Nonpareil almond both as to time and length. Color—white with pink tinge.

*Susceptibility or resistance to insects or diseases.*—Observations indicate that the variety is above average in resistance to brown rot and mite damage.

Crop:

*Productivity.*—Very heavy.

*Distribution of nuts on tree.*—Clusters on short spurs, also some on branches well distributed over the tree.

*Ripening period.*—Ripens with and after the Nonpareil almond.

*Harvest period.*—Harvests immediately after the Nonpareil almond.

*Tenacity.*—Hangs well on tree; easy to harvest and hull.

Hull: Smooth; thin.

*Suture.*—Flat.

*Dihiscence.*—Opens freely.

*Splitting.*—Along suture.

*Color.*—Grey-green (22–C–1), shading, as ripening progresses, to a lighter and somewhat yellow green (12–J–1).

Nut:

*Size.*—Average length, 29 mm. Average width, 18.8 mm. Average thickness, 16 mm. Average weight, .07 oz.

*Form.* — Length/width — 1.52 to 1 ratio ovate. Width/thickness—plump.

*Shell.* — Paper; thin. Outer shell — crumbling. Inner shell — soft; well sealed. Color — very light straw (9–B–2). Pits—small; numerous; deep; irregular.

*Base.*—Square.

*Stem scar.*—Small; obtuse.

*Apex.*—Acuminate; sharp; shouldered; tip recurved.

*Wing.*—Narrow; thin; tapered toward base.

*Inner surface.*—Light.

*Ventral streak.*—Dark; broad; long; point acute.

*Percentage of kernel to nut.*—58% to 63%.

Kernel:

*Size.*—Average length, 21⅘ mm. Average width, 12⅗ mm. Average thickness, 9⅖ mm. Average weight, .04 oz.

*Form.* — Length/width — ovate. Width/thickness—plump.

*Base.*—Ventrally oblique.

*Stem scar.*—Small; obtuse.

*Apex.*—Acute; shouldered.
*Pubescence.*—Smooth.
*Pellicle.*—Thin.
*Plumpness.*—Smooth.
*Color of skin.*—Light brown (12–K–8).
*Color of meat.*—White (9–A–1).
*Number of doubles.*—Few.
*Defective kernels.*—None.
*Flavor.*—Sweet.
*Quality.*—Very good.

The tree and its nuts herein described may vary in slight detail due to climatic and soil conditions under which the variety may be grown.

Having thus described my invention, I claim:

A new and distinct variety of almond tree, as shown and described, characterized by vigorous and upright growth of the tree and the heavy production of well distributed paper-shell nuts borne mainly in clusters on short spurs but in part on branches; and further characterized—in comparison to the Nonpareil almond—by being pollinizers for each other, by a parallel blooming period, by ripening with and after the Nonpareil and harvesting immediately following the latter, by at least twice the production of equal quality nuts, and by well sealed white meat nuts having a very light straw colored shell.

No references cited.